United States Patent
Sorrentino et al.

(10) Patent No.: US 6,447,803 B1
(45) Date of Patent: Sep. 10, 2002

(54) THICKENER-RHEOLOGY MODIFIER SYSTEM FOR PERSONAL CARE COMPOSITIONS

(75) Inventors: Paul M. Sorrentino, Monmouth Jct., NJ (US); Ian W. Cottrell, Princeton, NJ (US); Johan G. L. Pluyer, East Millstone, NJ (US); Tamara Babenko, Bridgewater, NJ (US)

(73) Assignee: National Starch and Chemical Investment Holding Corporation, New Castle, DE (US)

( * ) Notice: Subject to any disclaimer, the term of this patent is extended or adjusted under 35 U.S.C. 154(b) by 0 days.

(21) Appl. No.: 09/134,221

(22) Filed: Aug. 14, 1998

(51) Int. Cl.⁷ .............................. A61K 9/10; A61K 7/11; A61K 7/48; A61K 47/32; A61K 47/04
(52) U.S. Cl. .............. 424/487; 424/70.16; 424/DIG. 2; 514/844; 514/846; 514/944
(58) Field of Search .......................... 424/78.18, 70.16, 424/DIG. 2, 485–488; 514/844, 846, 772.4, 772.6, 777, 944; 510/119, 130

(56) References Cited

U.S. PATENT DOCUMENTS

| 4,384,096 A | 5/1983 | Sonnabend | 526/313 |
|---|---|---|---|
| 4,529,773 A | 7/1985 | Witiak et al. | 524/558 |
| 4,540,576 A | 9/1985 | Zahradnik | 424/151 |
| 4,616,074 A | 10/1986 | Ruffner | 526/318 |
| 4,743,698 A | 5/1988 | Ruffner et al. | 549/478 |
| RE33,156 E | 1/1990 | Shay et al. | 526/301 |
| 5,011,978 A | 4/1991 | Barron et al. | 560/221 |
| 5,294,692 A | 3/1994 | Barron et al. | 526/301 |
| 5,368,843 A | 11/1994 | Rennie | 424/49 |
| 5,549,914 A | 8/1996 | Farber | 424/487 |

FOREIGN PATENT DOCUMENTS

EP 0 786 514 7/1997 ............ C11D/1/66

OTHER PUBLICATIONS

G. Shay, "Alkali–Swellable and Alkali–Soluble Thickener Technology", American Chemical Society, 1989, pp. 457–493.

*Primary Examiner*—Edward J. Webman
(74) *Attorney, Agent, or Firm*—Karen G. Kaiser, Esq.

(57) ABSTRACT

A selected thickener-rheology modifier system comprising the combination of a hydrophobically, modified alkali-soluble thickener and a polysaccharide hydrocolloid or gum or polyalkylene glycol, preferably with a surfactant and more preferably with boric acid is especially useful in personal care compositions such as hair care and skin care compositions.

8 Claims, No Drawings

THICKENER-RHEOLOGY MODIFIER SYSTEM FOR PERSONAL CARE COMPOSITIONS

BACKGROUND OF THE INVENTION

This invention relates to a thickener-rheology modifier system for personal care compositions and particularly for hair and skin care compositions comprising the combination of a hydrophobically modified alkali-soluble thickener and a polysaccharide hydrocolloid or gum-type thickener or polyalkylene glycol, preferably with a surfactant and more preferably with boric acid.

Polymeric water-soluble thickening agents are widely known and used in many aqueous systems including coating applications, household and personal care products. Carboxyl-containing copolymers produced by the addition or free-radical polymerization of ethylenically unsaturated monomers and that swell or solubilize to thicken aqueous media on neutralization are commonly referred to as alkali-swellable or alkali-soluble thickeners. Hydrophobically modified or associative alkali-soluble thickeners have been developed to provide enhanced thickening properties. A description of alkali-soluble thickeners (AST) and associative AST's can be found in an American Chemical Society article by G. D. Shay entitled "Alkali-Swellable and Alkali-Soluble Thickener Technology", 1989, pp. 457–493.

While different thickeners including associative alkali-soluble thickeners have been disclosed in various applications, there still is the desire to find a system which provides suitable thickening as well as other rheological properties needed for personal care applications. This invention provides a thickener-rheology modifier system which significantly improves the thickening properties of alkali-swellable thickeners and also improves rheology characteristics of gel textures and emulsions from brittle/cuttable to more flowable, shear thinning and makes the products aesthetically acceptable for personal care use.

SUMMARY OF THE INVENTION

Now it has been found that a selected thickener-rheology modifier system comprising the combination of a hydrophobically, modified alkali-soluble thickener and a polysaccharide hydrocolloid or gum or polyalkylene glycol, preferably with a surfactant and more preferably with boric acid is especially useful in personal care compositions such as hair care and skin care compositions. These compositions which contain the thickener-rheology modifier system as described herein, provide the combination of improved thickening properties for alkali-swellable thickeners as well as improved rheology properties such as altered gel textures from brittle/cuttable to more flowable, shear thinning.

More particularly, this invention relates to a thickener-rheology modifier system for use in hair care and skin care compositions comprising:

a) a hydrophobically modified, alkali-soluble copolymer thickener comprising an aqueous emulsion copolymer of:

i) from about 5 to 70 weight percent of α, β, ethylenically unsaturated carboxylic acid monomer of the formula:

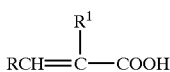

where R is H and $R^1$ is H, $C_1$–$C_4$ alkyl, or —$CH_2COOX$; R is —COOX and $R^1$ is H or —$CH_2COOX$; and R is $CH_3$ and $R^1$ is H, $C_1$–$C_4$ alkyl or —$CH_2COOX$; and X is H or $C_1$–$C_4$ alkyl;

ii) from about 10 to 90 weight percent of a nonionic, copolymerizable, α, β, ethylenically unsaturated monomer of the formula:

where Y is H or $CH_3$ and Z is

where R is $C_1$ to $C_4$ alkyl; and iii) from about 1 to 30 weight percent of a hydrophobically modified, α, β, ethylenically unsaturated carboxylic acid monomer of the formula:

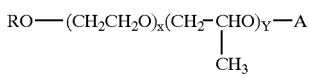

where R is an alkyl group of 6 to 22 carbon atoms or an alkaryl of 8 to 22 carbon atom, x is an average number of from about 6 to 200, y is an average number of from about 0 to 50 and A is residue of an unsaturated carboxylic acid having the formula:

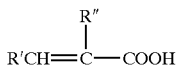

were R' is H, —COOH or $CH_3$ and R" is H, $CH_3$, —COOH or —$CH_2COOH$; and b) a polysaccharide hydrocolloid or gum or polyalkylene glycol.

Preferably the thickener-rheology modifier system will contain a surfactant and more preferably will contain boric acid.

DETAILED DESCRIPTION OF THE INVENTION

The thickener-rheology modifier system of this invention includes a hydrophobically modified alkali-soluble thickener (associative AST) which is an aqueous emulsion copolymer of i) an α, β ethylenically unsaturated carboxylic acid monomer; ii) a nonionic, copolymerizable α, β ethylenically unsaturated monomer and iii) a hydrophobically modified α, β ethylenically unsaturated carboxylic acid monomer.

The alkali soluble polymer thickener will comprise about 5 to 70 weight percent of an α, β ehtylenically unsaturated carboxylic acid monomer of the formula:

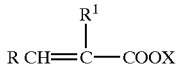

where R is H and $R^1$ is H, $C_1$–$C_4$ alkyl, or —$CH_2COOX$; R is —COOX and $R^1$ is H or —$CH_2$ COOX; and R is $CH_3$ and $R^1$ is H, $C_1$–$C_4$ alkyl or —$CH_2COOX$; and X is H is $C_1$–$C_4$ alkyl.

Examples of these acid monomers include acrylic, methacrylic, crotonic, acyloxypropionic, maleic, fumaric, itaconic, aconitic and half or mono esters of the dibasic or tribasic acids such as the monobutyl ester of maleic acid can also be used to advantage. Acrylic and methacrylic acid are preferred acid monomers. The preferred amount of these acid monomers is from about 30 to 50 percent by weight.

The nonionic, copolymerizable, α, β, ethylenically unsaturated monomer component of the alkali-soluble thickener has the formula:

where Y is H or $CH_3$ and Z is

where R is $C_1$ to $C_4$ alkyl.

Examples of these nonionic monomers are the $C_1$–$C_4$ alkyl acrylates and methacrylates such as methyl acrylate, ethyl acrylate, butyl acrylate, and ethyl methacrylate. The amount of nonionic monomer in the alkali-soluble copolymer will be from about 10 to 90 weight percent and preferably from about 30 to 70 weight percent.

The third monomer component of the alkali-soluble copolymer is a hydrophobically modified α, β ethylenically unsaturated carboxylic acid monomer of the formula:

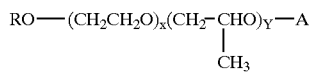

where R is an alkyl group of 6 to 22 carbon atoms or an alkaryl group of 8 to 22 carbon atoms, x is an average number of from about 6 to 100, y is an average number of from about 0 to 50 and A is the residue of an unsaturated carboxylic acid having the formula:

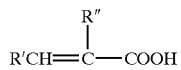

where R' is H, —COOH or $CH_3$ and R" is H, $CH_3$, —COOH or —$CH_2$COOH.

Preferably R in the hydrophobically modified carboxylic acid monomer will contain from 10 to 20 carbon atoms, x is an average number of 10 to 60 and y is an average number of 0 to 30 and A is acrylic, methacrylic or itaconic acid. The amount of the hydrophobically modified carboxylic acid monomer in the alkali-soluble copolymer will be from about 1 to 30 weight percent and preferably 5 to 20 weight percent.

The hydrophobically modified carboxylic acid monomers used in this invention and described above can be prepared by the conventional catalyzed esterification reaction of an alcohol with acid. Other known alternate esterification methods include alcoholysis and transesterification such as disclosed in U.S. Pat. No. 4,384,096.

The alkali-soluble copolymer thickener may be prepared by conventional emulsion polymerization techniques using appropriate emulsifiers for emulsifying the monomers and maintaining the polymer obtained in a stable-dispersed condition. A typical technique is described in U.S. Pat. No. 4,616,074 where the polymerization is carried out in continuous, semi-continuous or batch fashion with the polymerization reaction initiated at 40 to 90° C. A thermal decomposition initiator such as ammonium persulfate or potassium persulfate is used or at lower temperatures a redox initiator such as t-butyl hydroperoxide/bisulfite is used. An anionic emulsifier is normally included in the reaction medium at a concentration of about 1 to 3% to maintain a stable aqueous dispersion. Suitable emulsifiers include sodium lauryl sulfate, sodium dodecylbenzene sulfonate as well as other ammonium and alkali metal alkyl aryl sulfonates and alkyl sulfates. The polymerization is carried out at a pH below about 5.0 to maintain the insolubility of the copolymer in continuous water phase. The copolymer dispersions have relatively low viscosity even at solids content of from 20 to 40 weight percent or higher. Upon addition of an alkali to neutralize at least a portion of the free carboxyl groups, aqueous systems containing the copolymers markedly thicken. Any alkali may be used to neutralize the copolymers and may be an alkali metal hydroxide such as sodium or potassium hydroxide, sodium carbonate, or other bases such as ammonium hydroxide, methylamine, diethylamine, triethylamine and triethanolamine. Generally an effective neutralizing amount of alkali is used and depending on the particular application, it will be an amount sufficient to adjust the pH of the mixture to above 6.5. More particularly, the amount of neutralizing agent used will be an amount sufficient to adjust the pH of the mixture to from about 6.5 to 14 and preferably to from about 6.5 to 12. In hair care gel applications the pH is preferably adjusted to from about 6.5 to 10 and more preferably to from about 7.0 to 7.5.

Besides the hydrophobically modified alkali-soluble thickener, the thickener-rheology modifier system of this invention includes a polysaccharide hydrocolloid or gum type thickener or polyalkylene glycol. Additionally and preferably the thickener-rheology modifier system of this invention may include a surfactant and more preferably will include boric acid.

The polysaccharide hydrocolloids that are useful in this invention are those prepared from gums such as xanthan gum and its derivatives and guar gum as well as those derived from cellulose such as carboxyalkyl cellulose or hydroxyalkyl cellulose, more particularly those having alkyl of 1 to 4 carbon atoms such as carboxymethyl cellulose and hydroxyethyl cellulose. Xanthan gum is the particularly preferred polysaccharide hydrocolloid used in this invention. Also useful are the polyalkylene glycois, particularly those having alkylene groups of 2 to 4 carbon atoms such as polyethylene glycol, polypropylene glycol and polybutylene glycol and mixtures thereof. Molecular weight of the the polyalkylene glycol can vary from about 2000 to 14000 and preferably from about 2000 to 9000. Mixtures or blends of such polysaccharide hydrocolloids and polyalkylene glycols may also be used including combinations of one or more of xanthan gum, carboxymethyl cellulose, hydroxyethyl cellulose and polyethylene glycol.

The surfactant used as a separate preferred component besides the hydrophobically modified, alkali-soluble copolymer thickener and the polysaccharide hydrocolloid or polyalkylene glycol is a nonionic surfactant and more particularly hydrophobic nonionic surfactants having a hydrophilic-lipophilic balance (HLB) of from about 4 to 16. Surfactants of this type include Lauramida DEA, Polysorbate 81, Polysorbate 80, Nonoxynol-5, Ceteth-20, Steareth-20 and ethoxylate alcohol. Anionic surfactants that are anionic derivatives of fatty alcohol ethoxylates such as sodium lauryl sulfate and sodium laureth sulfate may also be used as the surfactant.

As noted above, the thickener-rheology modifier system of this invention preferably may also include boric acid besides the alkali-soluble thickener, polysaccharide hydrocolloid or poyalkylene glycol and the surfactant.

The thickener-rheology modifier system of this invention generally comprises an aqueous emulsion containing from about 0.1 to 6% by weight of the hydrophobically modified, alkali-soluble copolymer thickener, from about 0.05 to 2% by weight of the polysaccharide hydrocolloid or xanthan gum or poalkylene glycol, from about 0 to 20% by weight of nonionic or fatty alcohol ethoxylate surfactant and from about 0 to 0.1% by weight of boric acid. Preferably the system will include from about 0.1 to 20% by weight of the surfactant and more preferably will include from about 0.01 to 0.1% by weight of boric acid. The system will also include an alkali neutralizing agent in an effective amount to neutralize at least a portion of the free carboxyl groups and adjust the pH to from about 6.5 to 14 depending on the type of application. The balance of the system will comprise water. More particularly, the system will comprise from about 0.1 to 2.5% by weight of the alkali-soluble copolymer, from about 0.1 to 1% by weight of the polysaccharide hydrocolloid or polyalkylene glycol, from about 0.1 to 10% by weight of the surfactant, an effective neutralizing amount of alkali and the balance water. Preferably the system will also include from about 0.02 to 0.04% by weight of boric acid.

The thickener-rheology modifier system of this invention is useful in personal care compositions and more particularly in hair care and skin care compositions. These compositions will generally comprise at least one cosmetically-functional agent used in an amount effective to impart desired cosmetic properties to the personal care composition. The term "cosmetically-functional agent", as used herein, means any material, compound or composition applied to the hair or skin for cosmetic application thereof. Exemplary agents include emollients, humectants, lubricants, UV-light inhibitors, preservatives, pigments, dyes, colorants, alpha-hydroxy acids, aesthetic enhancers such as starch, perfumes and fragrances, film formers (water proofing agent), antiseptics, antifungal, antimicrobial and other medicaments, solvents, surfactants, natural or synthetic polymers, hair conditioning agents and hair fixatives. Such cosmetically-functional agents include mineral oils, glycerin, beeswax, lanolin, acetylated lanolin, stearic acid, palmitic acid, cetyl alcohol, sodium salts of olefin sulfonates, various proteins, polymeric sugars, conditioning agents such as polyquatemiun and hair fixatives such as poly(vinyl pyrrolidone) and N-vinyl formamide or polyvinyl formamide. These personal care compositions will more particularly comprise from about 0.1 to 20% by weight of one or more cosmetically-functional agents and preferably from about 0.1 to 10% of such agents.

The thickener-rheology modifier system of this invention is particularly useful in hair treatment compositions and more particularly in hair fixative gel compositions. These compositions provide improved thickening properties of alkali-swellable polymeric thickeners and also alter the gel textures from brittle/cuttable to more flowable, shear thinning. These hair care or hair gel compositions will generally comprise an effective amount of hair fixative polymer or component, and more particularly from about 0.1 to 20%, preferably from about 0.1 to 10% and more preferably from about 1 to 5% by weight. The thickener-rheology modifier system will make up the balance of the composition and this will comprise from about 0.1 to 6% by weight of the hydrophobically modified, alkali-soluble copolymer thickener, from about 0.05 to 2% by weight of polysaccharide hydrocolloid or polyalkylene glycol, from about 0 to 20% by weight of nonionic or fatty alcohol ethoxylate surfactant, from about 0 to 0.1% by weight of boric acid, an effective neutralizing amount of alkali and the balance water. Preferably the hair treatment or hair gel composition will comprise from about 0.1 to 10% of hair fixative polymer, from about 0.1 to 2.5% of hydrophobically modified, alkali-soluble thickener, from about 0.1 to 1% of the polysaccharide hydrocolloid or polyalkylene glycol, from about 0.1 to 10% of the surfactant, from about 0.02 to 0.04% of boric acid, an effective neutralizing amount of alkali and the balance water, with all percents by weight based on the weight of the composition.

Any hair fixative polymer which is effective in such purpose and is compatible with the thickener-rheology modifier system of this invention may be used in the hair treatment composition. Particularly useful hair fixatives that may be used include polyvinyl formamide, polyvinyl acetamide, poly(vinyl pyrrolidone), cationically modified polysaccharides (i.e., celluloses, starches, guars) and derivatives thereof.

The hair treatment compositions may further include other additives such as fragrance, preservatives, conditioners, colorants, plasticizers, emulsifiers, glossifiers, clarifiers, pearling agents, sequestering agents and other material or additives commonly used in hair fixative compositions. The hair care composition may contain from about 0.1 to 20 weight percent of one or more of these additives and preferably will comprise from 0.1 to 10% of one or more of these ingredients.

The following examples will further illustrate the embodiments of this invention. In these examples all parts are given by weight and all temperatures in degrees Celsius unless otherwise noted.

EXAMPLE 1

A thickener-rheology modifier composition was formulated using a hydrophobically modified alkali-soluble thickener made up of acrylic/methacrylic acids, acrylate/methacrylate esters and steareth-20 itaconate (hereinafter referred to as component or thickener A). The remainder of the thickener-rheology modifier system included xanthan gum, boric acid, the surfactant Neodol® 25.7 and a neutralizing agent triethanolamine.

The above prepared thickener-rheology modifier was formulated into a hair treatment composition (fixative gel) having the following composition:

| Hair Treatment Composition-1 | |
| --- | --- |
| Component | Amount |
| Polyvinyl Formamide (PVF) (10% solution) | 30.0 |
| Thickener A | 4.0 |
| Xanthan Gum | 0.2 |
| Boric Acid | 0.03 |
| Neodol (R) 25.7 | 0.1 |
| Triethanolamine | 0.93 |
| Dowicil 200 | 0.1 |
| Deionized Water | q.s. |

The above prepared hair gel composition was subject to several subjective evaluations as well as rheological studies. The studies were compared to similar hair gel compositions, one containing only thickener A as part of the thickener-rheology system (i.e., without xanthan gum, boric acid and Neodol surfactant) and another comparative sample which contained Carbopol 940, a polyacrylic copolymer, instead of the four component thickener-rheology system described above.

The subjective evaluations included a stretchability test, (how well sample elongates with applied force), a flowability test (how well sample flows when applying force without forming globules), a rigidity or memory test (how well product yields or holds its form, or is it supple and returns to its prior form quickly), and a cutability test (ability to slice/break into sections, portions, segments). These evaluations were made by a panel of eight people. The systems were also studied using a controlled stress rheometer (Carri-Med CSL100) in order to compare viscosities as well as visco-elastic properties of composition 1 versus the controls.

In all subjective evaluations the hair treatment composition-1 containing the thickener-rheology system as described was observed to provide the Theological properties of stretchability, flowability, rigidity and cutability which were significantly better than the composition which contained only thickener A (i.e., without xanthan gum, boric acid or Neodol surfactant). A further comparison of hair treatment composition-1 with a similar composition containing the control thickener Carbomer instead of the four component thickener-rheology modifier system showed that the rheological properties were very comparable.

EXAMPLE 2

A cosmetic lotion containing a hydrophobically modified alkali-soluble thickener made up of acrylic/methacrylic acids, acrylate/methacrylate esters and steareth-20 itaconate (hereinafter referred to as component or thickener A) was formulated and had the following ingredients:

| Component | Parts by Weight |
| --- | --- |
| Deionized water | 50.0 |
| Xanthan gum | 0.1 |
| Isostearyl alcohol | 4.7 |
| Cetearyl alcohol | 1.0 |
| Ceteareth-20 | 0.5 |
| Hydrogenated coco-glycerides | 8.3 |
| Glyceryl stearate | 2.0 |
| Thickener A | 1.65 |
| Deionized Water | q.s. |
| Sodium hydroxide | q.s. to pH >6.5 |

This formulation provided an aesthetically pleasing and acceptable product which had good skin-feel and rheology.

EXAMPLE 3

A cosmetic body wash containing a hydrophobically modified alkali-soluble thickener made of acrylic/methacrylic acids, acrylate/methacrylate esters and steareth-20 itaconate (hereinafter referred to as component or thickener A) was formulated and had the following ingredients:

| Component | Parts by Weight |
| --- | --- |
| Xanthan gum | 0.1 |
| Sodium laureth sulfate | 0.2 |
| Thickener A | 1.65 |
| Sodium hydroxide | q.s. pH >6.5 |

This formulation provided an aesthetically pleasing and acceptable cosmetic product which had good skin-feel and rheology.

EXAMPLE 4

A styling hair gel composition was formulated containing a hyrdrophobically modified alkali-soluble thickener made up of acrylic/methacrylic acids, acrylate/methacrylate esters and steareth-20 itaconate (hereinafter referred to as component or thickener A) and having the following ingredients:

| Components | Parts by Weight |
| --- | --- |
| Thickener A | 4.5 |
| Tetrasodium EDTA | 0.01 |
| Polyethylene glycol (MW 7000) | 0.1 |
| Glycerin | 1.0 |
| Dimethicone copolyol | 0.2 |
| Polyvinylpyrrolidone | 2.0 |
| Deionized water | q.s. |
| Triethanolamine | q.s. to pH 6.5 to 8.5 |

This hair gel formulation provided good rheological and thickening properties and was aesthetically acceptable for personal care use.

What is claimed is:
1. A thickener-rheology modifier system comprising
  a) from about 0.1 to 6% by weight of a hydrophobically modified, alkali-soluble copolymer thickener comprising an aqueous emulsion copolymer of:
    i) from about 5 to 70 weight percent based on the weight of thickener of an $\alpha$, $\beta$ ethylenically unsaturated carboxylic acid monomer of the formula:

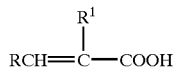

where R is H and $R^1$ is H, $C_1$–$C_4$ alkyl, or —$CH_2COOX$; R is —COOX and $R^1$ is H or —$CH_2COOX$ and R is $CH_3$ and $R^1$ is H, $C_1$–$C_4$ alkyl or —$CH_2COOX$; and X is H or $C_1$–$C_4$ alkyl;
    ii) from about 10 to 90 weight percent based on the weight of thickener of a nonionic copolymerizable, $\alpha$, $\beta$ ethylenically unsaturated monomer of the formula:

$$CH_2{=}CYZ$$

where Y is H or $CH_3$ and Z is

where R is $C_1$–$C_4$ alkyl; and
    iii) from about 1 to 30 weight percent based on the weight of thickener of a hydrophobically modified, $\alpha$, $\beta$ ethylenically unsaturated carboxylic acid monomer of the formula:

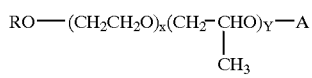

where R is an alkyl group of 6 to 22 carbon atoms or an alkayl of 8 to 22 carbon atoms, x is an average number of from about 6 to 100, y is an average number of from about 0 to 50 and A is the residue of an unsaturated carboxylic acid having the formula:

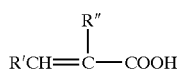

were R' is H, —COOH or $CH_3$ and R" is H, $CH_3$, —COOH or —$CH_2COOH$
  b) from about 0.05 to 2% by weight of a polysaccharide hydrocolloid or polyalkylene glycol;
  c) an effective neutralizing amount of alkali;
  d) from about 0 to 20% of a non-ionic or fatty alcohol ethoxylate surfactant e) from about 0.02 to 0.1% by weight boric acid; and f) the balance water.

2. The thickener-rheology modifier system of claim 1, wherein the surfactant is a hydrophobic nonionic surfactant having an HLB of 4 to 16 or an anionic surfactant which is a derivative of fatty alcohol ethoxylates.

3. The thickener-rheology modifier system of claim 2, wherein the boric acid is present in an amount of from about 0.02 to 0.04% by weight.

4. The thickener-rheology modifier system of claim 3 wherein the polysaccharide hydrocolloid is xanthan gum.

5. The thickener-rheology modifier system of claim 4 which comprises from about 0.1 to 2.5% by weight of the alkali-soluble copolymer, from about 0.1 to 1% by weight of xanthan gum, from about 0.1 to 10% by weight of surfactant and from about 0.02 to 0.04% by weight of boric acid.

6. The thickener-rheology modifier system of claim 3 wherein the alkali-soluble copolymer thickener comprises from about 30 to 50 weight percent based on the weight of thickener of unsaturated carboxylic acid monomer i); from about 30 to 70 weight percent based on the weight of thickener of nonionic monomer ii) and from about 5 to 20 weight percent based on the weight of thickener of hydrophobically modified carboxylic acid monomer iii).

7. The thickener-rheology modifier system of claim 6 which comprises from about 0.1 to 2.5% by weight of the alkali-soluble copolymer and from about 0.1 to 1% by weight of polysaccharide hydrocolloid or polyalkylene glycol.

8. The thickener-rheology modifier system of claim 7 wherein the polysaccharide hydrocolloid is xanthan gum.

* * * * *